US011590360B2

(12) United States Patent
Liu et al.

(10) Patent No.: US 11,590,360 B2
(45) Date of Patent: *Feb. 28, 2023

(54) METHOD FOR ANALYZING ELEMENTS AND MASS RATIOS OF ELEMENTS OF TISSUE AND METHOD FOR ESTABLISHING GEOMETRIC MODEL BASED ON MEDICAL IMAGE

(71) Applicant: NEUBORON MEDTECH LTD., Jiangsu (CN)

(72) Inventors: Yuan-Hao Liu, Jiangsu (CN); Ming-Chen Hsiao, Jiangsu (CN)

(73) Assignee: NEUBORON MEDTECH LTD., Nanjing (CN)

( * ) Notice: Subject to any disclaimer, the term of this patent is extended or adjusted under 35 U.S.C. 154(b) by 846 days.

This patent is subject to a terminal disclaimer.

(21) Appl. No.: 16/439,980

(22) Filed: Jun. 13, 2019

(65) Prior Publication Data
US 2019/0329067 A1    Oct. 31, 2019

Related U.S. Application Data (63) Continuation of application No. PCT/CN2017/092745, filed on Jul. 13, 2017.

(30) Foreign Application Priority Data

Jan. 11, 2017   (CN) .......................... 201710017476.X (51) Int. Cl.
*A61N 5/10* (2006.01)
*G16H 30/40* (2018.01)
(Continued)

(52) U.S. Cl.
CPC ............ *A61N 5/1031* (2013.01); *A61B 6/032* (2013.01); *G06T 17/00* (2013.01); *G16H 30/40* (2018.01);
(Continued)

(58) Field of Classification Search
CPC ...... A61N 5/10–1084; A61N 2005/1085–1098
See application file for complete search history.

(56) References Cited

U.S. PATENT DOCUMENTS

2007/0282575 A1   12/2007  Gossage
2017/0301085 A1*  10/2017  Riklin Raviv .......... G16Z 99/00
2018/0247452 A1    8/2018  Liu et al.

FOREIGN PATENT DOCUMENTS

CN   101751697 A   6/2010
CN   104267425 A   1/2015
(Continued)

OTHER PUBLICATIONS

International Search Report of PCT/CN2017/092745, dated Sep. 30, 2017.
(Continued)

*Primary Examiner* — Thaddeus B Cox
(74) *Attorney, Agent, or Firm* — Locke Lord LLP; Tim Tingkang Xia, Esq.

(57) ABSTRACT

A process for analyzing elements and mass ratios of elements of a tissue includes approximating the tissue having unknown elements and mass ratios of the unknown elements thereof using the data of the medical image corresponding to a tissue having known elements and mass ratios of the known elements thereof. A method for establishing a geometric model based on a medical image includes: reading data of the medical image; defining a type of a tissue according to a conversion relationship between the data of the medical image and tissue types or according to the process; determining a quantity of tissue clusters of the tissue; defining a tissue density of the tissue by a conversion relationship between the data of the medical image and density values; establishing a 3D coding matrix with information about the tissue and the density; and generating the geometric model.

20 Claims, 4 Drawing Sheets

(51) Int. Cl.
*A61B 6/03* (2006.01)
*G06T 17/00* (2006.01)

(52) U.S. Cl.
CPC ............... *A61N 2005/109* (2013.01); *A61N 2005/1034* (2013.01); *G06T 2210/41* (2013.01)

(56) References Cited

FOREIGN PATENT DOCUMENTS

| CN | 104537699 A | 4/2015 |
|---|---|---|
| CN | 106474634 A | 3/2017 |
| EP | 1658878 A1 | 5/2006 |
| EP | 3378534 A1 | 9/2018 |
| JP | 2012088771 A | 5/2012 |
| TW | 201720374 A | 6/2017 |
| TW | 201722357 A | 7/2017 |
| TW | 201722358 A | 7/2017 |

OTHER PUBLICATIONS

Barbara Vanderstraeten et al., Conversion of CT numbers into tissue parameters for Monte Carlo dose calculations: a multi-centre study, Physics in Medicine and Biology, 52 (2007) 539-562.

Wilfried Schneider et al., Correlation between CT numbers and tissue parameters needed for Monte Carlo simulations of clinical dose distributions, Phys. Med. Biol. 45 (2000) 459-478.

\* cited by examiner

METHOD FOR ANALYZING ELEMENTS AND MASS RATIOS OF ELEMENTS OF TISSUE AND METHOD FOR ESTABLISHING GEOMETRIC MODEL BASED ON MEDICAL IMAGE

CROSS-REFERENCE TO RELATED PATENT APPLICATION

This application is a continuation application of International Application No. PCT/CN2017/092745, filed on Jul. 13, 2017, which claims priority to Chinese Patent Application No. 201710017476.X, filed on Jan. 11, 2017, the disclosures of which are hereby incorporated by reference.

FIELD

The present disclosure relates to a method for analyzing elements and mass ratios of the elements of a tissue and a method for establishing a geometric model, and more particularly to a method for analyzing elements and mass ratios of elements of a tissue based on medical image and a method for establishing a geometric model based on medical image.

BACKGROUND

The background description provided herein is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

As atomics moves ahead, such radiotherapy as Cobalt-60, linear accelerators and electron beams has been one of major means to cancer therapy. However, conventional photon or electron therapy has been undergone physical restrictions of radioactive rays; for example, many normal tissues on a beam path will be damaged as tumor cells are destroyed. On the other hand, sensitivity of tumor cells to the radioactive rays differs greatly, so in most cases, conventional radiotherapy falls short of treatment effectiveness on radioresistant malignant tumors (such as glioblastoma multiforme and melanoma).

For the purpose of reducing radiation damage to the normal tissue surrounding a tumor site, target therapy in chemotherapy has been employed in the radiotherapy. While for high-radioresistant tumor cells, radiation sources with high RBE (relative biological effectiveness) including such as proton, heavy particle and neutron capture therapy have also developed. Among them, the neutron capture therapy combines the target therapy with the RBE, such as the boron neutron capture therapy (BNCT). By virtue of specific grouping of boronated pharmaceuticals in the tumor cells and precise neutron beam regulation, BNCT is provided as a better cancer therapy choice than conventional radiotherapy.

BNCT takes advantage that the boron ($^{10}B$)-containing pharmaceuticals have high neutron capture cross section and produces $^4He$ and $^7Li$ heavy charged particles through $^{10}B(n,\alpha)^7Li$ neutron capture and nuclear fission reaction. The total range of the two particles approximately amounts to a cell size. Therefore, radiation damage to living organisms may be restricted at the cells' level. When the boronated pharmaceuticals are gathered in the tumor cells selectively, only the tumor cells will be destroyed locally with a proper neutron source on the premise of having no major normal tissue damage.

Three-dimensional model is widely used in scientific experiment analysis, scientific experiment simulation field. For example, in the field of nuclear radiation and protection, in order to simulate the dose absorbed by the living organisms under certain radiation conditions, it is often necessary to process the medical image by using computer technology to establish an accurate lattice model required by Monte Carlo software and combine with the software for simulation calculations.

At present, the Monte Carlo method is a tool that can accurately simulate the collision trajectory and energy distribution of the nuclear particle in the three-dimensional space of the irradiated target. The combination of the Monte Carlo method with a complex three-dimensional human anatomy model represents a leap forward of simulation in computer technology. In diagnostic radiographic examination, accurate human organ dose assessment is very beneficial for radiation therapy. At present around the world, a variety of human models have been successfully established and combined with Monte Carlo simulation program to evaluate the accuracy of the human body's absorbed dose in the radiation environment. It is a prerequisite for Monte Carlo simulation to successfully transform the three-dimensional anatomical model of human body into geometric description required by Monte Carlo program. It is also the hot and difficult point of Monte Carlo simulation in the world at present.

Medical image such as Magnetic Resonance Imaging (MRI) or Computed Tomography (CT) can provide detailed tissue geometry information for human body features, providing data basis for physical modeling of human internal structures. Wherein, taking computed tomography as an example, the CT image data is converted into a voxel phantom model similar to the human anatomy, thereby simulating the migration history of the radiation and the action on the human tissues to calculate the radiation absorbed dose. Therefore, when given the elements composition of the voxel phantom, they are as close as possible to the actual situation of the patient, so as to obtain the closest result to the real situation in the simulation calculation. However, the current definition of materials for voxel phantom is generally defined by that a fixed-range of CT values corresponds to a tissue of fixed elements composition ratio, as described in a literature published by Vanderstraeten et al. in 2007 (described in more details thereinafter), CT value=−100~20 corresponds to fat, and CT value=20~100 corresponds to muscle. However, the human body tissues should be composed of specific elements mass ratio instead of the fixed elements mass ratio in a single interval. It should be seen that there are still considerable room for improvement in the current common voxel phantom component definition method.

Therefore, it is necessary to propose a method for analyzing elements mass ratio of a tissue and a method for establishing a geometric model including the analysis method based on medical image to improve the accuracy of the treatment plan.

SUMMARY

An aspect of the present disclosure provides a method for analyzing elements and mass ratios of the elements of a tissue based on medical image, including approximating the tissue having unknown elements and mass ratios of the unknown elements thereof using the data of the medical image corresponding to a tissue having known elements and mass ratios of the known elements thereof. The method uses the known elements and the mass ratios of the known elements of a tissue to calculate the unknown elements and the mass ratios of the known elements of other tissues with the corresponding data of the medical image, and provides more tissue types for establishing a voxel phantom based on medical image conversion. The phantom may be used in the Monte Carlo treatment planning system to specify the correct physical action data, such as the linear attenuation coefficient of photons, the effective cross section of neutrons, and the mass blocking power of charged particles (protons, electrons or other charged particles), in Monte Carlo calculations through a large amount of elements mass ratio of tissues, and provide a near-real particle migration environment.

Implementations of this aspect may include one or more of the following features.

More particularly, the data of medical image may be related to a photon linear attenuation coefficient, and an effective linear attenuation coefficient of the tissue having known elements and mass ratios of the elements thereof may be obtained from the medical image data thereof.

Further, the tissue having unknown elements and mass ratios of the unknown elements thereof is approximated using the data of the medical image corresponding to the tissue having known elements and the mass ratios of the known elements thereof includes:

calculating an average linear attenuation coefficient $\mu_i$ under a beam of the medical image by weighting a plurality of photon linear attenuation coefficients of basic elements provided by NIST using a beam energy spectrum of the medical image;

obtaining an efficiency weighting factor C as a product of a detector efficiency and an additive factor of the medical image, and correcting a linear attenuation coefficient $\mu_{tissue}$ of each of a plurality of tissues by the efficiency weighting factor C to obtain an effective linear attenuation coefficient $\mu_{\it eff}$ of each of the tissues, wherein $\mu_{\it eff} = C \cdot \mu_{tissue} = C \cdot \Sigma_{i=1}^{n} m_i \mu_i$;

obtaining a mass ratio distribution of chemical elements $m_i$ in a living organism corresponding to each of the data of the medical image by a derivation algorithm using the mass ratios of elements of a tissue with similar data of the medical image as an initial hypothesis.

More particularly, the data of the medical image may be CT values, and the relationship between a Hounsfield unit (HU) of the CT values and the effective linear attenuation coefficient $\mu_{\it eff}$ is $HU=1000(\mu_{\it eff}/\mu_{water}-1)$, and the CT values may be grouped into a plurality of groups with a size of n, and the CT values range from −100 to +1530 may be divided into 1630/n groups. The derivation algorithm may be a maximum approximation algorithm.

Another aspect of the present disclosure provides a method for establishing a geometric model based on medical image, including:

reading data of the medical image;
defining a type of a tissue according to a conversion relationship between the data of the medical image and tissue types or according to the method for analyzing elements and mass ratios of the elements of the tissue based on the medical image disclosed above;
determining a quantity of tissue clusters of the tissue;
defining a tissue density of the tissue by a conversion relationship between the data of the medical image and density values;
establishing a 3D encoding matrix with information about the tissue and the tissue density; and
generating the geometric model based on the 3D encoding matrix.

The method for establishing the geometric model is based on a conversion relationship between medical image data and tissue type. The quantity of tissue clusters may be determined according to actual requirements, so that the tissue type, the element composition and the density are provided more accurately, and the geometric model being established is better matched to the real situation reflected by the data of the medical image.

Implementations of this aspect may include one or more of the following features.

More particularly, the method for establishing the geometric model may be applied to neutron capture therapy and further includes assigning a Boron-10 concentration and establishing the 3D encoding matrix with Boron-10 concentration information. The geometric model labeled with Boron-10 concentration information clearly shows that the concentration of the boron-containing drug in each tissue and then when performing neutron capture therapy simulation, it is more realistic to reflect the actual situation.

The quantity of the tissue clusters is a quantity of the tissue clusters manually defined by a user, plus a quantity of four tissue clusters, fourteen tissue clusters or seventy tissue clusters already existing in a database or a quantity of 163 tissue clusters determined by the method for analyzing the mass ratios of elements of a tissue. If there is no established corresponding quantity of the tissue clusters in the existing database, a new quantity of the tissue clusters can be defined by the user. This avoids the situation where only approximate choices can be made if the corresponding quantity of the tissue clusters cannot be exactly matched in an existing database, thereby effectively improving the accuracy of the modeling.

More particularly, the method for establishing the geometric model further includes establishing a 3D tissue encoding matrix and establishing a 3D density encoding matrix. According to the slice of the medical image data, the corresponding tissue encoding and density encoding are established for each slice through the corresponding transformation relations so as to establish the 3D tissue encoding matrix and the 3D density encoding matrix.

The geometric model includes a lattice card, a cell card, a surface card and a material card required by the input file of MCNP software. Through the medical image data, the lattice cards, cell card, surface card and material card required by the input file of MCNP software are finally obtained, which provide a theoretical basis for simulation calculation and obtain accurate simulation results.

In yet another aspect of the present disclosure provides a method for establishing a geometric model based on medical image, the method including: reading data of the medical image; defining or reading a region of interest (ROI) boundary; determining whether each of a plurality of medical image voxels in the data of the medical image is within the ROI boundary; when one of the medical image voxels is determined to be within the ROI boundary, performing manually defining a type and a density of a ROI tissue by assigning a particular tissue and the density to the one of the medical image voxels within the ROI boundary, or performing: automatically defining the type of the ROI tissue according to a conversion relationship between the data of the medical image and tissue types or the method for analyzing elements and mass ratios of the elements of a tissue based on the medical image disclosed above, determining a quantity of tissue clusters of the ROI tissue, and automatically defining the density of the ROI tissue by a conversion relationship between the data of the medical image and density values; when one of the medical image voxels is determined not to be within the ROI boundary, performing automatically defining the type of the tissue according to the conversion relationship between the data of the medical image data and the tissue types or the method for analyzing the elements and the mass ratios of the elements of a tissue based on the medical image disclosed above, determining the quantity of the tissue clusters of the tissue, and automatically defining the tissue density of the tissue by the conversion relationship between the data of the medical image and the density values; establishing a 3D encoding matrix with information about the tissue and the tissue density; and generating the geometric model based on the 3D encoding matrix.

The so-called ROI is the region of interest (hereinafter collectively referred to as ROI), the user can manually define the tissue type, elements composition and density of ROI. If the medical image voxel is not within the ROI boundary, the definition of the tissue type is performed according to the conversion relationship between the medical image data and the tissue type, and the number of tissue clusters is determined according to the actual needs so as to provide the tissue type, the element composition and the density more accurately, and the established geometric model more closely matches the real situation reflected by the medical image data.

Implementations of this aspect may include one or more of the following features.

More particularly, the method for establishing the geometric model may be applied to neutron capture therapy and further includes assigning a Boron-10 concentration and establishing the 3D encoding matrix with Boron-10 concentration information. The geometric model labeled with Boron-10 concentration information clearly shows that the concentration of the boron-containing drug in each tissue and then when performing neutron capture therapy simulation, it is more realistic to reflect the actual situation.

The quantity of the tissue clusters is a quantity of the tissue clusters manually defined by a user, plus a quantity of four tissue clusters, fourteen tissue clusters or seventy tissue clusters already existing in a database or a quantity of 163 tissue clusters determined by the method for analyzing the elements and the mass ratios of the elements of a tissue. If there is no established corresponding quantity of the tissue clusters in the existing database, a new quantity of the tissue clusters can be defined by the user. This avoids the situation where only approximate choices can be made if the corresponding quantity of the tissue clusters cannot be exactly matched in an existing database, thereby effectively improving the accuracy of the modeling.

More particularly, the method for establishing the geometric model further includes establishing a 3D tissue encoding matrix and establishing a 3D density encoding matrix. According to the slice of the medical image data, the corresponding tissue encoding and density encoding are established for each slice through the corresponding transformation relations so as to establish the 3D tissue encoding matrix and the 3D density encoding matrix.

The geometric model includes a lattice card, a cell card, a surface card and a material card required by the input file of MCNP software. Through the medical image data, the lattice cards, cell card, surface card and material card required by the input file of MCNP software are finally obtained, which provide a theoretical basis for simulation calculation and obtain accurate simulation results.

Medical image data may be Magnetic Resonance Imaging (MRI), Computed Tomography (CT), Positron Emission Tomography (PET), PET-CT or X-ray imaging. The following embodiments will be described based on the data of Computed Tomography, the file format of which is usually DICOM. However, it is well known to those skilled in the art that other medical image data may also be used, as long as the medical image data may be converted into a voxel phantom tissue model, it may be applied to the method for analyzing elements mass ratio of a tissue and the method for establishing a geometric model based on medical image data disclosed by the present disclosure.

The method for analyzing elements and mass ratios of elements of a tissue and the method for establishing a geometric model based on the medical image disclosed by the present disclosure analyzes the elements and the mass ratios of the elements of living tissues through the medical image data of the known tissues, and it may directly correspond to the composition of each element in the living tissues according to the CT values, so that the voxel phantom may be more realistic to the real situation when made, thereby improving the accuracy of the dose calculation to improve the quality of treatment.

Further areas of applicability will become apparent from the description provided herein. It should be understood that the description and specific examples are intended for purposes of illustration only and are not intended to limit the scope of the present disclosure.

BRIEF DESCRIPTION OF THE DRAWINGS

The accompanying drawings illustrate one or more embodiments of the disclosure and together with the written description, serve to explain the principles of the disclosure. Wherever possible, the same reference numbers are used throughout the drawings to refer to the same or like elements of an embodiment.

DETAILED DESCRIPTION OF THE DISCLOSURE

The embodiments of the present disclosure are further described in detail below with reference to the accompanying drawings, so that those skilled in the art can implement the technical solutions according to the description.

In certain embodiments, a method for analyzing elements and mass ratios of the elements of a tissue and a method for establishing a geometric model based on medical image for neutron capture therapy may be taken as embodiments of the present disclosure. The following will briefly introduce neutron capture therapy, especially boron neutron capture therapy.

Neutron capture therapy (NCT) has been increasingly practiced as an effective cancer curing means in recent years, and BNCT is the most common. Neutrons for NCT may be supplied by nuclear reactors or accelerators. Take AB-BNCT for example, its principal components include, in general, an accelerator for accelerating charged particles (such as protons and deuterons), a target, a heat removal system and a beam shaping assembly. The accelerated charged particles interact with the metal target to produce the neutrons. Suitable nuclear reactions are always determined according to such characteristics as desired neutron yield and energy, available accelerated charged particle energy and current and materialization of the metal target, among which the most discussed two are $^7$Li (p, n) $^7$Be and $^9$Be (p, n) $^9$B and both are endothermic reaction. Their energy thresholds are 1.881 MeV and 2.055 MeV respectively. Epithermal neutrons at a keV energy level are considered ideal neutron sources for BNCT. Theoretically, bombardment with lithium target using protons with energy slightly higher than the thresholds may produce neutrons relatively low in energy, so the neutrons may be provided clinically without many moderations. However, Li (lithium) and Be (beryllium) and protons of threshold energy exhibit not high action cross section. In order to produce sufficient neutron fluxes, high-energy protons are usually selected to trigger the nuclear reactions.

Figure 1:
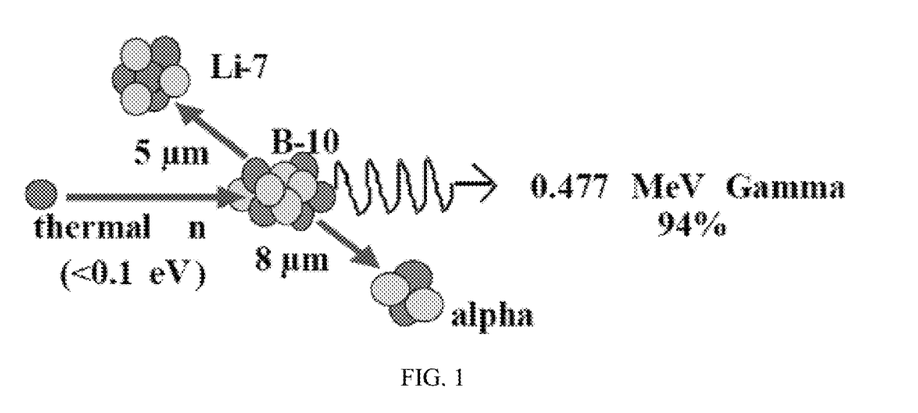
FIG. 1 is a schematic view of boron neutron capture reaction.
Figure 2:
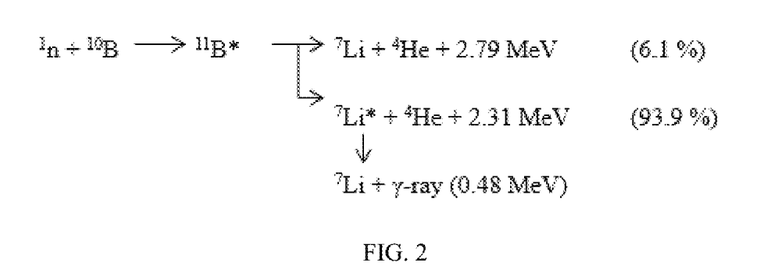
FIG. 2 is a nuclear reaction formula of $^{10}B(n,\alpha)\ ^{7}Li$ neutron capture.

BNCT takes advantage that the boron ($^{10}$B)-containing pharmaceuticals have high neutron capture cross section and produces $^4$He and $^7$Li heavy charged particles through $^{10}$B(n,α)$^7$Li neutron capture and nuclear fission reaction. As illustrated in FIGS. 1 and 2, a schematic drawing of BNCT and a nuclear reaction formula of $^{10}$B(n,α) $^7$Li neutron capture are shown, the two charged particles, with average energy at about 2.33 MeV, are of linear energy transfer (LET) and short-range characteristics. LET and range of the alpha particle are 150 keV/μm and 8 μm respectively while those of the heavy charged particle $^7$Li are 175 keV/μm and 5 μm respectively, and the total range of the two particles approximately amounts to a cell size. Therefore, radiation damage to living organisms may be restricted at the cells' level. When the boronated pharmaceuticals are gathered in the tumor cells selectively, only the tumor cells will be destroyed locally with a proper neutron source on the premise of having no major normal tissue damage.

In neutron capture therapy, in order to simulate the absorbed dose of an organism under certain radiation conditions to help doctors to develop a treatment plan, it is often necessary to process the medical image using computer technology to establish an accurate lattice model required by Monte Carlo software and perform simulation calculations combined with the software. The purpose of the embodiments of the present disclosure is to establish a method for analyzing elements and mass ratios of the elements of a tissue based on medical image and a method for establishing a geometric model including the analysis method which may be closely similar to the structure of living tissues for tissue dose simulation calculation of boron neutron capture therapy. Medical image data may be Magnetic Resonance Imaging (MRI), Computed Tomography (CT), Positron Emission Tomography (PET), PET-CT or X-ray imaging. The present embodiments will be described based on the data of Computed Tomography, the file format of which is usually DICOM. However, it is well known to those skilled in the art that other medical image data may also be used as long as the medical image data may be converted into a voxel phantom model, it may be applied to the method for analyzing elements and mass ratios of elements of a tissue and the method for establishing a geometric model based on a medical image disclosed by the present disclosure.

The method for analyzing elements and the mass ratios of the elements of a tissue of the embodiment of the present disclosure is based on the relationship between the mass ratio distribution of chemical elements in the living organisms and the CT value. The CT value, also known as the Hounsfield Unit (HU or H), is the ratio of the linear attenuation coefficient of each tissue to that of water and is the unit representing light attenuation coefficient, which is defined as Formula 1:

$$HU = 1000\left(\frac{\mu_{eff}}{\mu_{water}} - 1\right) \quad \text{Formula 1}$$

The sum of products of the mass ratio of each element ($m_i$; $0 \le m_i \le 1$) and the linear attenuation coefficient of each element ($\mu_i$) is defined as the linear attenuation coefficient of each tissue ($\mu_{tissue} = \Sigma_{i=1}^n m_i\mu_i$). Using photon linear attenuation coefficients of the basic elements provided by the National Institute of Standards and Technology (NIST), the linear attenuation coefficients of each element in the energy range of the X-rays generated by CT are weighted and summed to obtain an average linear attenuation coefficient as the linear attenuation coefficient ($\mu_i$) of each element calculated in the present embodiment. The product of the detector efficiency and the enhancement factor in the CT scanner is provided as the efficiency weighting factor C to correct the linear attenuation coefficient of each tissue to become an effective linear attenuation coefficient of each tissue, i.e., $\mu_{eff} = C \cdot \mu_{tissue} = C \cdot \Sigma_{i=1}^n m_i\mu_i$. The literature published by W. Schneider et al. in 2000 (W. Schneider, T. Bortfeld, and W. Schlegel, "Correlation between CT numbers and tissue parameters needed for Monte Carlo simulations of clinical dose distributions", Phys. Med. Biol. 45, 459-478 (2000)) is taken as a standard, which lists the various elements ratio distribution of soft tissue or bone tissue corresponding to 70 CT values (effective linear attenuation coefficient), as shown in Table 1 below. Although the literature has listed the mass ratio of the elements of tissue corresponding to the specific CT value, the number of CT values that can be defined is still small, and some numerical intervals are large, making it difficult to accurately define values within the interval. Therefore, in the embodiment of the present disclosure, the mass ratios of the elements of the tissue with similar CT values may be taken as an initial hypothesis, and the mass ratio distribution of chemical elements, i.e., mi, in the living organisms corresponding to each CT value, may be obtained by a derivation algorithm, so that the elements composition ratio corresponding to each voxel unit may be obtained according to the CT image data, and then the three-dimensional voxel phantom model may be established to perform the treatment plan simulation based on the Monte Carlo algorithm. In this embodiment, the MCNP software may be used for the simulation.

TABLE 1

CT values correspond to 70 tissues composed of different elements (% by weight of elements)

| | | | | | $w_i$(pp) | | | | |
|---|---|---|---|---|---|---|---|---|---|
| | H | ρ (g cm$^{-3}$) | H | C | N | O | P | Ca | Others |
| Soft tissue | | | | | | | | | |
| Lung, blood-filled | −741 | 0.26 | 10.3 | 10.5 | 3.1 | 74.9 | 0.2 | | 1.0 |
| Adipose tissue 3 | −98 | 0.93 | 11.6 | 68.1 | 0.2 | 19.8 | | | 0.3 |
| Adipose tissue 2 | −77 | 0.95 | 11.4 | 59.8 | 0.7 | 27.8 | | | 0.3 |
| Adipose tissue 1 | −55 | 0.97 | 11.2 | 51.7 | 1.3 | 35.5 | | | 0.3 |
| Mammary gland 1 | −37 | 0.99 | 10.9 | 50.6 | 2.3 | 35.8 | 0.1 | | 0.3 |
| Mammary gland 2 | −1 | 1.02 | 10.6 | 33.2 | 3.0 | 52.8 | 0.1 | | 0.3 |
| Brain, cerebrospinal fluid | 13 | 1.01 | 11.1 | | | 88.0 | | | 0.9 |
| Adrenal gland | 14 | 1.03 | 10.6 | 28.4 | 2.6 | 57.8 | 0.1 | | 0.5 |
| Small intestine (wall) | 23 | 1.03 | 10.6 | 11.5 | 2.2 | 75.1 | 0.1 | | 0.5 |
| Urine | 26 | 1.02 | 11.0 | 0.5 | 1.0 | 86.2 | 0.1 | | 1.2 |
| Gallbladder bile | 27 | 1.03 | 10.8 | 6.1 | 0.1 | 82.2 | | | 0.8 |
| Lymph | 29 | 1.03 | 10.8 | 4.1 | 1.1 | 83.2 | | | 0.8 |
| Pancreas | 32 | 1.04 | 10.6 | 16.9 | 2.2 | 69.4 | 0.2 | | 0.7 |
| Prostate | 34 | 1.04 | 10.5 | 8.9 | 2.5 | 77.4 | 0.1 | | 0.6 |
| Brain, white matter | 34 | 1.04 | 10.6 | 19.4 | 2.5 | 66.1 | 0.4 | | 1.0 |
| Testis | 36 | 1.04 | 10.6 | 9.9 | 2.0 | 76.6 | 0.1 | | 0.8 |
| Brain, grey matter | 40 | 1.04 | 10.7 | 9.5 | 1.8 | 76.7 | 0.3 | | 1.0 |
| Muscle, skeletal 1 | 40 | 1.05 | 10.1 | 17.1 | 3.6 | 68.1 | 0.2 | | 0.9 |
| Stomach | 41 | 1.05 | 10.4 | 13.9 | 2.9 | 72.1 | 0.1 | | 0.6 |
| Heart 1 | 41 | 1.05 | 10.3 | 17.5 | 3.1 | 68.1 | 0.2 | | 0.8 |
| Kidney 1 | 41 | 1.05 | 10.2 | 16.0 | 3.4 | 69.3 | 0.2 | 0.1 | 0.8 |
| Thyroid | 42 | 1.05 | 10.4 | 11.9 | 2.4 | 74.5 | 0.1 | | 0.7 |
| Aorta | 43 | 1.05 | 9.9 | 14.7 | 4.2 | 69.8 | 0.4 | 0.4 | 0.6 |
| Heart 2 | 43 | 1.05 | 10.4 | 13.9 | 2.9 | 71.8 | 0.2 | | 0.8 |
| Kidney 2 | 43 | 1.05 | 10.3 | 13.2 | 3.0 | 72.4 | 0.2 | 0.1 | 0.8 |
| Liver 1 | 43 | 1.05 | 10.3 | 15.6 | 2.7 | 70.1 | 0.3 | | 1.0 |
| Muscle, skeletal 2 | 43 | 1.05 | 10.2 | 14.3 | 3.4 | 71.0 | 0.2 | | 0.9 |
| Muscle, skeletal 3 | 44 | 1.05 | 10.2 | 11.2 | 3.0 | 74.5 | 0.2 | | 0.9 |
| Heart 3 | 45 | 1.05 | 10.4 | 10.3 | 2.7 | 75.6 | 0.2 | | 0.8 |
| Mammary gland 3 | 45 | 1.06 | 10.2 | 15.8 | 3.7 | 69.8 | 0.1 | | 0.4 |
| Kidney 3 | 46 | 1.05 | 10.4 | 10.6 | 2.7 | 75.2 | 0.2 | 0.1 | 0.8 |
| Ovary | 46 | 1.05 | 10.5 | 9.3 | 2.4 | 76.8 | 0.2 | | 0.8 |
| Eye, lens | 49 | 1.07 | 9.6 | 19.5 | 5.7 | 64.6 | 0.1 | | 0.5 |
| Liver 2 | 53 | 1.06 | 10.2 | 13.9 | 3.0 | 71.6 | 0.3 | | 1.0 |
| Trachea | 54 | 1.06 | 10.1 | 13.9 | 3.3 | 71.3 | 0.4 | | 1.0 |
| Spleen | 54 | 1.06 | 10.3 | 11.3 | 3.2 | 74.1 | 0.3 | | 0.8 |
| Heart, blood filled | 56 | 1.06 | 10.3 | 12.1 | 3.2 | 73.4 | 0.1 | | 0.9 |
| Blood, whole | 56 | 1.06 | 10.2 | 11.0 | 3.3 | 74.5 | 0.1 | | 0.9 |
| Liver 3 | 63 | 1.07 | 10.1 | 12.6 | 3.3 | 72.7 | 0.3 | | 1.0 |
| Skin 1 | 72 | 1.09 | 10.0 | 25.0 | 4.6 | 59.4 | 0.1 | | 0.9 |
| Skin 2 | 74 | 1.09 | 10.0 | 20.4 | 4.2 | 64.5 | 0.1 | | 0.8 |
| Skin 3 | 77 | 1.09 | 10.1 | 15.8 | 3.7 | 69.5 | 0.1 | | 0.8 |
| Connective tissue | 100 | 1.12 | 9.4 | 20.7 | 6.2 | 62.2 | | | 1.5 |
| Skeletal tissue | | | | | | | | | |
| Yellow marrow | −49 | 0.98 | 11.5 | 64.4 | 0.7 | 23.1 | | | 0.3 |
| Yellow/red marrow (1:1) | −22 | 1.00 | 11.0 | 52.9 | 2.1 | 33.5 | 0.1 | | 0.4 |
| Red marrow | 11 | 1.03 | 10.5 | 41.4 | 3.4 | 43.9 | 0.1 | | 0.7 |
| Cartilage | 102 | 1.1 | 9.6 | 9.9 | 2.2 | 74.4 | 2.2 | | 1.7 |
| Sternum | 385 | 1.25 | 7.8 | 31.6 | 3.7 | 43.8 | 4.0 | 8.5 | 0.6 |
| Sacrum (male) | 454 | 1.29 | 7.4 | 30.2 | 3.7 | 43.8 | 4.5 | 9.8 | 0.6 |
| D6, L3 incl. cartilage (male) | 466 | 1.3 | 7.3 | 26.5 | 3.6 | 47.3 | 4.8 | 9.8 | 0.7 |
| Whole vertebral column (male) | 514 | 1.33 | 7.1 | 25.8 | 3.6 | 47.2 | 5.1 | 10.5 | 0.7 |
| D6, L3 excl. cartilage (male) | 526 | 1.33 | 7.0 | 28.7 | 3.8 | 43.7 | 5.1 | 11.1 | 0.6 |
| Humerus, spherical head | 538 | 1.33 | 7.1 | 37.9 | 2.6 | 34.2 | 5.6 | 12.2 | 0.4 |
| Femur, spherical head | 538 | 1.33 | 7.1 | 37.9 | 2.6 | 34.2 | 5.6 | 12.2 | 0.4 |
| Femur, conical trochanter | 586 | 1.36 | 6.9 | 36.6 | 2.7 | 34.7 | 5.9 | 12.8 | 0.4 |
| C4 incl. cartilage (male) | 599 | 1.38 | 6.6 | 24.3 | 3.7 | 47.1 | 5.7 | 11.9 | 0.7 |
| Sacrum (female) | 621 | 1.39 | 6.6 | 27.1 | 3.8 | 43.5 | 5.8 | 12.5 | 0.7 |
| Humerus, whole specimen | 636 | 1.39 | 6.7 | 35.2 | 2.8 | 35.2 | 6.2 | 13.5 | 0.4 |
| Ribs 2nd, 6th (male) | 657 | 1.41 | 6.4 | 26.3 | 3.9 | 43.6 | 6.0 | 13.1 | 0.7 |
| Innominate (male) | 658 | 1.41 | 6.3 | 26.2 | 3.9 | 43.6 | 6.1 | 13.2 | 0.7 |
| C4 excl. cartilage (male) | 672 | 1.42 | 6.3 | 26.1 | 3.9 | 43.6 | 6.1 | 13.3 | 0.7 |
| Femur (total bone) | 688 | 1.42 | 6.3 | 33.3 | 2.9 | 36.2 | 6.6 | 14.3 | 0.4 |
| Femur (whole specimen) | 702 | 1.43 | 6.3 | 33.1 | 2.9 | 36.3 | 6.6 | 14.4 | 0.4 |
| Innominate (female) | 742 | 1.46 | 6.0 | 25.0 | 3.9 | 43.5 | 6.6 | 14.3 | 0.7 |
| Clavicle, scapula | 756 | 1.46 | 6.0 | 31.3 | 3.1 | 37.0 | 7.0 | 15.2 | 0.4 |
| Humerus (total bone) | 756 | 1.46 | 6.0 | 31.4 | 3.1 | 36.9 | 7.0 | 15.2 | 0.4 |
| Humerus, cylindrical shaft | 805 | 1.49 | 5.8 | 30.1 | 3.2 | 37.4 | 7.2 | 15.8 | 0.5 |
| Ribs 10th (male) | 843 | 1.52 | 5.6 | 23.5 | 4.0 | 43.4 | 7.2 | 15.6 | 0.7 |
| Cranium | 999 | 1.61 | 5.0 | 21.2 | 4.0 | 43.5 | 8.1 | 17.6 | 0.6 |
| Mandible | 1113 | 1.68 | 4.6 | 19.9 | 4.1 | 43.5 | 8.6 | 18.7 | 0.6 |

TABLE 1-continued

CT values correspond to 70 tissues composed of different elements (% by weight of elements)

|  | H | ρ (g cm$^{-3}$) | H | C | N | O | P | Ca | Others |
|---|---|---|---|---|---|---|---|---|---|
| | | | \multicolumn{7}{c|}{w$_i$(pp)} | | | | | | |

| | H | ρ (g cm$^{-3}$) | H | C | N | O | P | Ca | Others |
|---|---|---|---|---|---|---|---|---|---|
| Femur, cylindrical shaft | 1239 | 1.75 | 4.2 | 20.4 | 3.8 | 41.5 | 9.3 | 20.2 | 0.6 |
| Cortical bone | 1524 | 1.92 | 3.4 | 15.5 | 4.2 | 43.5 | 10.3 | 22.5 | 0.6 |

Figure 3:
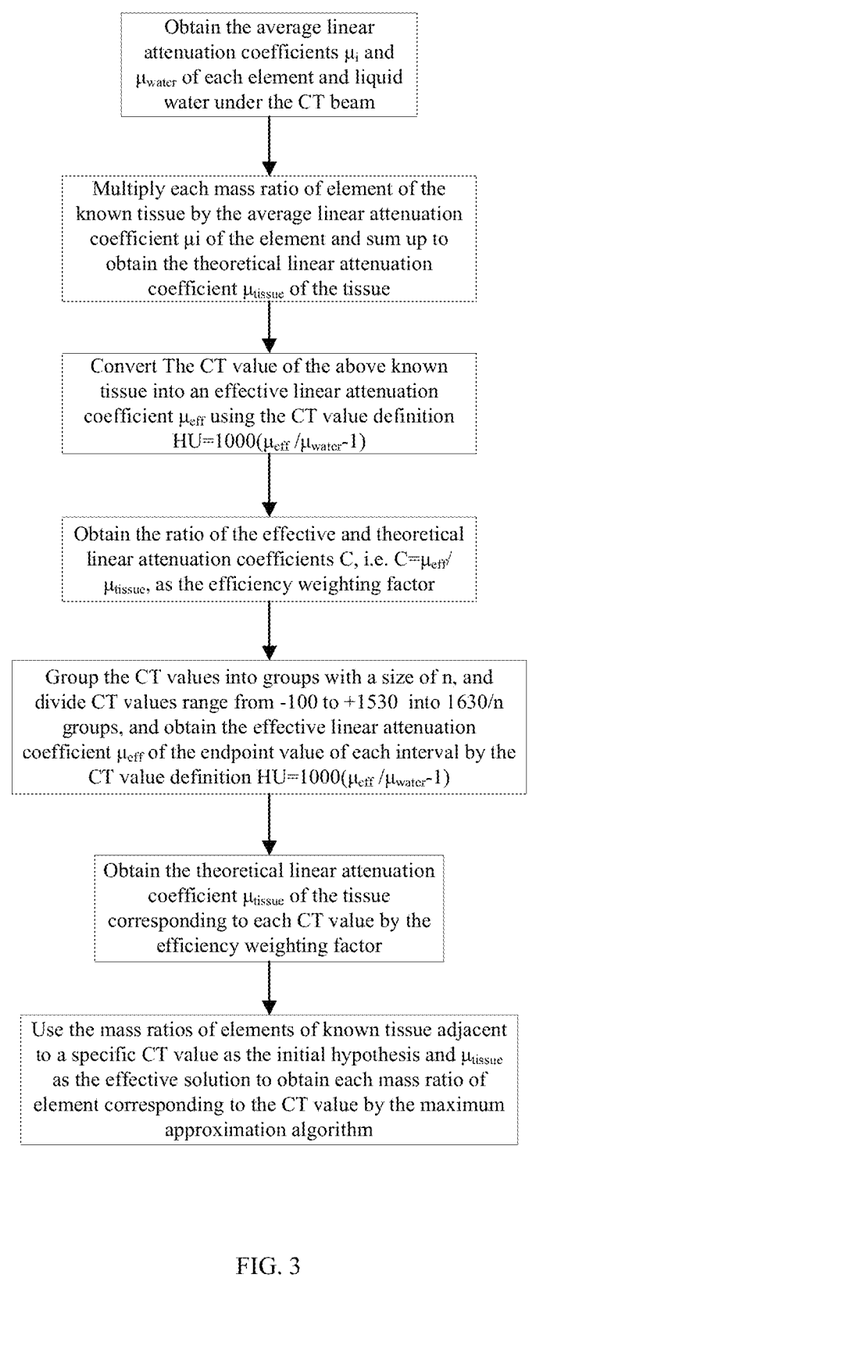
FIG. 3 is a logic block diagram of a method for analyzing mass ratios of elements of a tissue based on a medical image according to an embodiment of the present disclosure.

Referring to FIG. 3, the method for analyzing elements and mass ratios of the elements of a tissue based on the medical image disclosed in the embodiment of the present disclosure mainly includes the following processes:

1. The photon linear attenuation coefficients of the basic elements provided by NIST is weighted by the CT beam energy spectrum, and the average linear attenuation coefficients $\mu_i$ $\mu_{water}$ of each element and liquid water under the CT beam are obtained.

2. The literature published by W. Schneider et al. in 2000 is used as a standard, the CT values and the corresponding mass ratios of the elements of the 70 soft tissues and bone tissues may be obtained. The theoretical linear attenuation coefficient $\mu_{tissue}$ of a tissue (any one of the tissues in Table 1 in the embodiment) may be obtained by multiplying each known element and mass ratios of the known elements of the tissue (called the known tissue) by the average linear attenuation coefficient $\mu_i$ of the element and summing up.

3. The CT value of the above known tissue is converted into an effective linear attenuation coefficient $\mu_{eff}$ using the CT value definition HU=1000($\mu_{eff}/\mu_{water}$−1).

4. The ratio of the effective and theoretical linear attenuation coefficients C, i.e. C=$\mu_{eff}/\mu_{tissue}$, is obtained as the efficiency weighting factor, which includes the calculator tomographic detector efficiency and the additive factor in the calculator tomography process.

5. The CT values may be grouped into multiple groups with a size of n, and CT values range from −100 to +1530 may be divided into 1630/n groups. In the embodiment, n is 10, and a total of 163 groups, starting from −100. The effective linear attenuation coefficient $\mu_{eff}$ of the endpoint value of each interval is obtained by the CT value definition HU=1000($\mu_{eff}/\mu_{water}$−1), and then substituted into the formula C=$\mu_{eff}/\mu_{tissue}$ to obtain the theoretical linear attenuation coefficient $\mu_{tissue}$ of the tissue corresponding to the CT value.

6. Using the known mass ratios of the elements of tissue adjacent to a specific CT value as the initial hypothesis, each element mass ratio is multiplied by the average linear attenuation coefficient $\mu_i$ of the element and then is summed up. Taking the theoretical linear attenuation coefficient of the tissue $\mu_{tissue}$ corresponding to the CT value as an effective solution, each mass ratio of the element corresponding to the CT value may be obtained by the derivation algorithm, thereby perfecting the mass ratios of the elements of the 163 group organism tissues. The derivation algorithm is a maximum approximation algorithm in the embodiment.

Briefly, the method for establishing a geometric model based on medical image data disclosed in the embodiments of the present disclosure mainly includes the following processes:

1. A computed tomography image (in DICOM format) is input, and the CT image will be presented on the corresponding interface;

2. The defined ROI boundary in the DICOM file is automatically read, or a new ROI may also be added;

3. The software will determine the location of each voxel on the CT image and classify all voxels as "falling within the ROI boundary" and "falling outside the ROI boundary";

4. For the voxels inside the ROI boundary, according to the actual needs, the relative unique tissue type and tissue density for each ROI may be manually defined by a user, or the CT value may be automatically matched with the tissue type and density, so as to avoid the error of dose calculation because of assigning unique tissue type (elemental composition) and density of ROI which covers a wide range of CT values (e.g. mucosal chamber);

5. For the voxels outside the ROI boundary, the tissue type is automatically defined, and it may be distinguished into 4 or 14 or 70 or 163 tissues consisted of different elements according to the difference of the CT values, and the user may choose to use the four tissues listed in the ICRU-46 Report Form, as detailed below, or the fourteen tissues consisting of different elements published in 2007 by Vanderstraeten et al., as detailed below, or the seventy tissues composed of different elements in the literature published in 2000 by W. Schneider et al., or the 163 tissues obtained by the above-described method for analyzing elements and mass ratios of the elements of tissue disclosed in the present disclosure, depending on the actual judgment;

6. For the voxel of which the density has not been manually defined, the density will be assigned automatically according to the difference of the CT values, and a total of 96 density clusters may be distinguished;

7. The user manually inputs parameters such as a boron-containing drug concentration in normal blood, a tumor-blood boron concentration ratio, a tissue-blood boron concentration ratio and the like, and compiles the Boron-10 element into all the voxels;

8. The software will integrate the information such as the tissue type (elemental composition), tissue density, tissue Boron-10 concentration and the like to generate three-dimensional MCNP lattice model, and compile a lattice card, a cell card, a surface card, and a material card in MCNP input file format.

Figure 4:
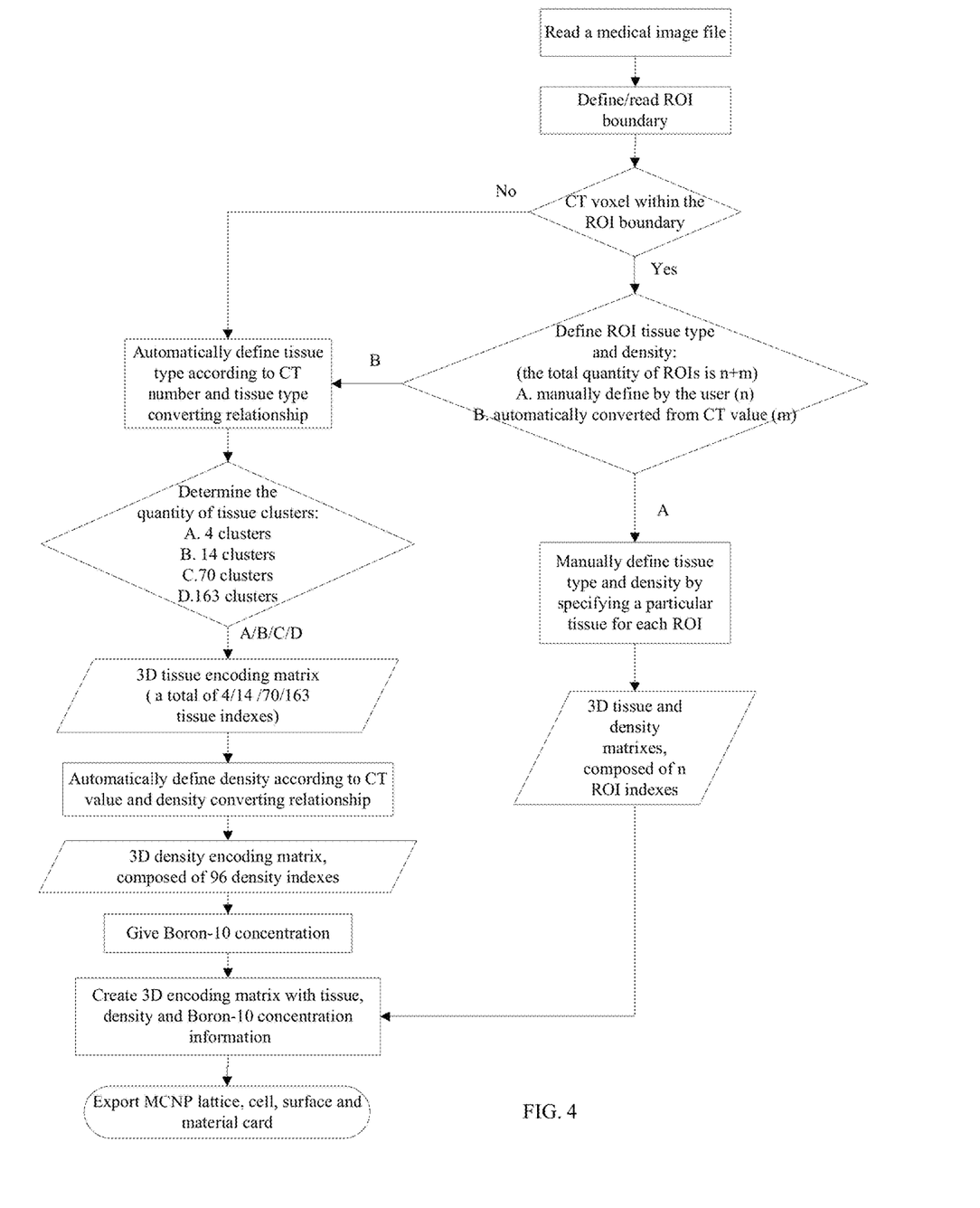
FIG. 4 is a logic block diagram of a method for establishing a geometric model based on a medical image according to an embodiment of the present disclosure.

Specifically, referring to FIG. 4, the method for establishing a geometric model based on medical image data disclosed by the present disclosure includes two embodiments.

One aspect of the present disclosure is to provide a method for establishing a geometric model based on medical image data, the method including: reading medical image data; defining a tissue type by a conversion relationship between the medical image data and the tissue type; determining the quantity of tissue clusters; defining a tissue density by a conversion relationship between the medical image data and the tissue density; establishing 3D encoding matrix with information about the tissue and the density; and generating a geometric model.

According to a conversion relationship between medical image data and a tissue type, the quantity of tissue clusters may be determined according to actual requirements, so that the tissue type, the element composition and the density may be provided more accurately, and an established geometric model may be better matched to the real situation reflected by the medical image data.

The method for establishing a geometric model further includes assigning a Boron-10 concentration and establishing a 3D encoding matrix with Boron-10 concentration information. The geometric model labeled with Boron-10 concentration information clearly shows that the concentration of the boron-containing drug in each tissue and then when performing neutron capture therapy simulation, it may be more realistic to reflect the actual situation.

The quantity of the t may be the quantity of the tissue clusters manually defined by the user plus the four tissue clusters or fourteen tissue clusters or seventy tissue clusters already existing in the database or 163 tissue clusters determined by the method for analyzing elements and mass ratios of the elements of a tissue according to the present disclosure. If there is no established corresponding quantity of the tissue clusters in the existing database, a new quantity of the tissue clusters may be defined by the user. This avoids the situation where only approximate choices may be made if the corresponding quantity of the tissue clusters cannot be exactly matched in an existing database, thereby effectively improving the accuracy of the modeling.

The method for establishing a geometric model further includes establishing a 3D tissue encoding matrix and establishing a 3D density encoding matrix. According to the slice of the medical image data, the corresponding tissue encoding and density encoding may be established for each slice through the corresponding transformation relations so as to establish the 3D tissue encoding matrix and the 3D density encoding matrix.

The geometric model includes a lattice card, a cell card, a surface card and a material card required by the input file of MCNP software. Through the medical image data, the lattice cards, cell card, surface card and material card required by the input file of MCNP software are finally obtained, which provide a theoretical basis for simulation calculation and obtain accurate simulation results.

Another aspect of the present disclosure is to provide a method for establishing a geometric model based on medical image data, the method including: reading medical image data; defining or reading an ROI boundary; determining whether a medical image voxel is within an ROI boundary; if yes, then performing manually defining a tissue type and density by assigning a particular tissue and density to voxels within each ROI boundary or performing automatically defining a ROI tissue type and density by a conversion relationship between the medical image data and the tissue type/density, if no, then performing automatically defining a tissue type by a conversion relationship between the medical image data and the tissue type, and defining a tissue density by a conversion relationship between the medical image data and the density; establishing 3D encoding matrix with information about the tissue and the density; and generating a geometric model.

The so-called ROI refers to the region of interest. Users may manually define the tissue type, element composition, and density of the ROI. If the medical image voxel is not within the ROI boundary, the definition of the tissue type is performed according to the conversion relationship between the medical image data and the tissue type/density, and the quantity of tissue clusters may be determined according to the actual needs so as to provide the tissue type, the element composition and the density more accurately, and the established geometric model more closely matches the real situation reflected by the medical image data.

The method for establishing a geometric model further includes assigning a Boron-10 concentration and establishing a 3D encoding matrix with Boron-10 concentration information. The geometric model labeled with Boron-10 concentration information clearly shows that the concentration of the boron-containing drug in each tissue and then when performing neutron capture therapy simulation, it may be more realistic to reflect the actual situation.

The quantity of the tissue clusters is the quantity of the tissue clusters manually defined by the user, plus a quantity of the four tissue clusters or fourteen tissue clusters or seventy tissue clusters already existing in the database or a quantity of 163 tissue clusters determined by the method for analyzing elements and mass ratios of the elements of a tissue disclosed above according to the present disclosure. If it covers a wide range of CT values within a single ROI boundary (e.g. mucosal chamber), the CT value may be automatically matched with the tissue type and density, so as to avoid the error of dose calculation because of assigning unique tissue type (elemental composition) and density. If there is no established corresponding quantity of the tissue clusters in the existing database, a new quantity of the tissue clusters may be defined by the user. This avoids the situation where only approximate choices may be made if the corresponding quantity of the tissue clusters cannot be exactly matched in an existing database, thereby effectively improving the accuracy of the modeling.

The method for establishing a geometric model further includes establishing a 3D tissue encoding matrix and establishing a 3D density encoding matrix. According to the slice of the medical image data, the corresponding tissue encoding and density encoding may be established for each slice through the corresponding transformation relations so as to establish the 3D tissue encoding matrix and the 3D density encoding matrix.

The geometric model includes a lattice card, a cell card, a surface card and a material card required by the input file of MCNP software. Through the medical image data, the lattice cards, cell card, surface card and material card required by the input file of MCNP software are finally obtained, which provide a theoretical basis for simulation calculation and obtain accurate simulation results.

Figure 5:
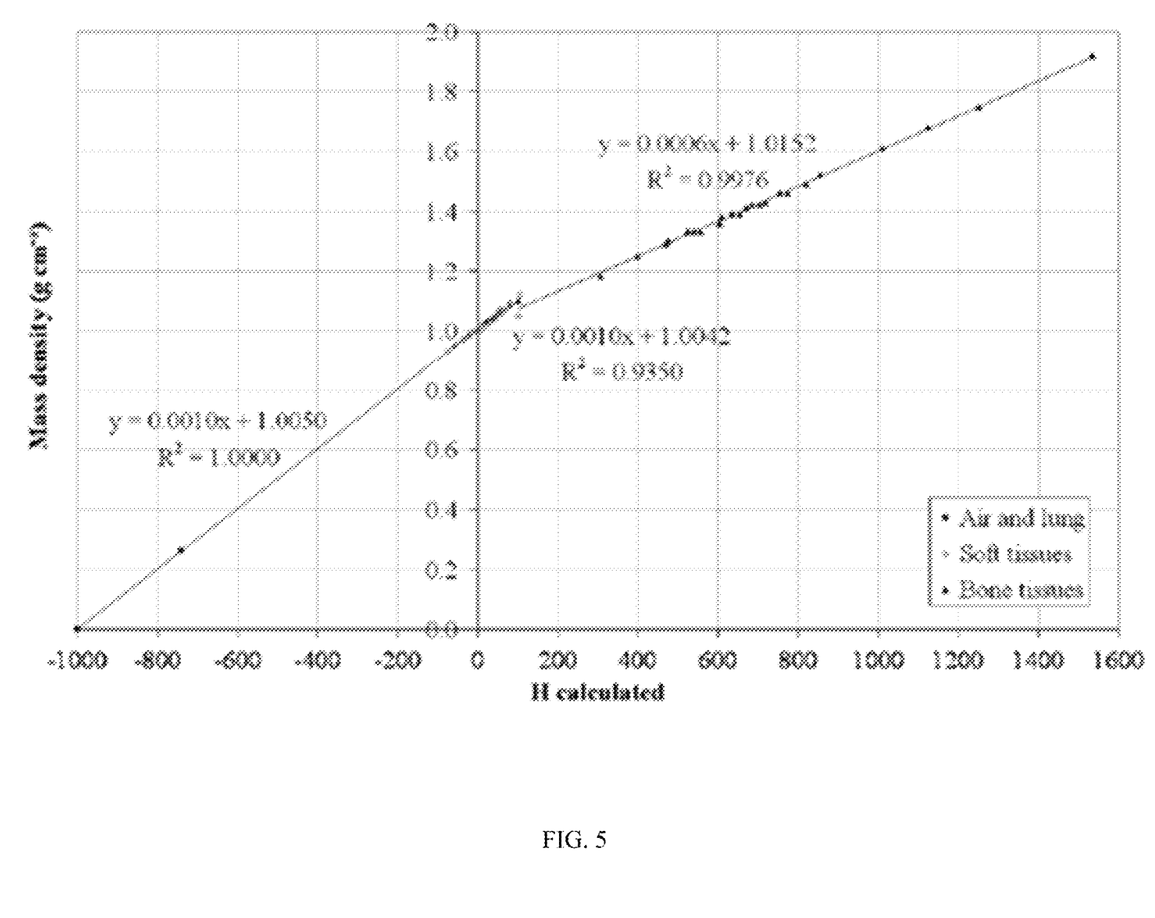
FIG. 5 is a chart showing regression curve formula and correlation coefficient of CT value (HU) and tissue density.

Referring to FIG. 5, the CT value—tissue type and CT value—tissue density conversion charts in the existing database in the method for establishing a geometric model based on medical image data disclosed in the present disclosure will be described below.

Reference was made to the literature published by Vanderstraeten et al. in 2007 (Barbara Vanderstraeten et al, "Conversion of CT numbers into tissue parameters for Monte Carlo dose calculations: a multi-center study", Phys. Med. Biol. 52 (2007) 539-562.), depending on the CT values, they can be converted into one type of air, one type of lung, two types of soft tissues (adipose and muscle) and ten types of bones, in other words, different CT values correspond to a total of 14 tissues consisted of different elements, as shown in Table 2 below.

TABLE 2

CT values correspond to 14 tissues composed of different elements (% by weight of elements)

| tissue | HU | H | C | N | O | Na | Mg | P | S | Cl | Ar | K | Ca |
|---|---|---|---|---|---|---|---|---|---|---|---|---|---|
| air | <-900 | | | 75.5 | 23.2 | | | | | | 1.3 | | |
| lung | -900~-100 | 10.3 | 10.5 | 3.1 | 74.9 | 0.2 | | 0.2 | 0.3 | 0.3 | | 0.2 | |
| adipose | -100~20 | 11.2 | 53.3 | 1.1 | 34.1 | 0.1 | | | 0.1 | 0.1 | | | |
| muscle | 20~100 | 10.1 | 15.6 | 4.0 | 69.3 | 0.3 | | 0.1 | 0.3 | 0.2 | | 0.1 | |
| bone | 100~250 | 9.5 | 45.3 | 2.5 | 35.5 | 0.1 | | 2.1 | 0.2 | 0.1 | | 0.1 | 4.6 |
| bone | 250~400 | 8.4 | 40.1 | 2.8 | 36.9 | 0.1 | 0.1 | 3.6 | 0.2 | 0.1 | | 0.1 | 7.7 |
| bone | 400~550 | 7.5 | 35.5 | 3.0 | 38.1 | 0.1 | 0.1 | 4.8 | 0.2 | 0.1 | | 0.1 | 10.5 |
| bone | 550~700 | 6.7 | 31.6 | 3.3 | 39.2 | 0.1 | 0.1 | 5.9 | 0.2 | 0.1 | | | 12.8 |
| bone | 700~850 | 6.0 | 28.1 | 3.5 | 40.1 | 0.1 | 0.1 | 6.8 | 0.2 | | | | 14.9 |
| bone | 850~1000 | 5.3 | 25.0 | 3.7 | 41.0 | 0.1 | 0.1 | 7.7 | 0.3 | | | | 16.8 |
| bone | 1000~1150 | 4.8 | 22.3 | 3.8 | 41.7 | 0.1 | 0.2 | 8.4 | 0.3 | | | | 18.4 |
| bone | 1150~1300 | 4.3 | 19.8 | 4.0 | 42.3 | 0.1 | 0.2 | 9.1 | 0.3 | | | | 19.9 |
| bone | 1300~1450 | 3.8 | 17.6 | 4.1 | 42.9 | 0.1 | 0.2 | 9.7 | 0.3 | | | | 21.2 |
| bone | >1450 | 3.4 | 15.6 | 4.2 | 43.5 | 0.1 | 0.2 | 10.3 | 0.3 | | | | 22.4 |

Reference was made to Report No. ICRU-46 (International Commission on Radiation Units and Measurements, Photon, electron, proton and neutron interaction data for body tissues, ICRU-46, Tech. Rep., 1992.), and four major human brain tissues were taken, including air, adult brain, adult skin and cranium, with the corresponding density and elemental composition shown in Table 3.

TABLE 3

CT values corresponding to four tissues composed of different elements (% by weight of elements)

| tissue | ρ (g/cm³) | H | C | N | O | Na | Mg | P | S | Cl | Ar | K | Ca |
|---|---|---|---|---|---|---|---|---|---|---|---|---|---|
| air | 0.001293 | | | 75.5 | 23.2 | | | | | | 1.3 | | |
| adult brain | 1.04 | 10.7 | 14.5 | 2.2 | 71.2 | 0.2 | | 0.4 | 0.2 | 0.3 | | 0.3 | |
| adult skin | 1.09 | 10.0 | 20.4 | 4.2 | 64.5 | 0.2 | | 0.1 | 0.2 | 0.3 | | 0.1 | |
| cranium | 1.61 | 5.6 | 21.2 | 4.0 | 43.5 | 0.1 | 0.2 | 8.1 | 0.3 | | | | 17.6 |

The same reference was made to the literature of Vanderstraeten et al., which unified the true experimental values from hospitals, and sorted out the relationship formula of CT value corresponding to tissue density, as shown in FIG. 5; the geometric model establishment method based on medical image data disclosed in the present disclosure used the three sets of regression formulas in FIG. 5 to classify CT values (−1000 to 2000) into 96 density clusters, as shown in Table 4.

TABLE 4

Conversion of CT value and mass density HUL and HUU being the lower and upper limits of CT value, respectively

| $HU_L$ | $HU_U$ | ρ (g/cm³) |
|---|---|---|
| | −990 | 0.0050 |
| −990 | −980 | 0.0200 |
| −980 | −970 | 0.0300 |
| −970 | −960 | 0.0400 |
| −960 | −950 | 0.0500 |
| −950 | −925 | 0.0675 |
| −925 | −900 | 0.0925 |
| −900 | −875 | 0.1175 |
| −875 | −850 | 0.1425 |
| −850 | −825 | 0.1675 |
| −825 | −800 | 0.1925 |
| −800 | −775 | 0.2175 |
| −775 | −750 | 0.2425 |
| −750 | −725 | 0.2675 |
| −725 | −700 | 0.2925 |

TABLE 4-continued

Conversion of CT value and mass density HUL and HUU being the lower and upper limits of CT value, respectively

| $HU_L$ | $HU_U$ | ρ (g/cm³) |
|---|---|---|
| −700 | −650 | 0.3300 |
| −650 | −600 | 0.3800 |
| −600 | −550 | 0.4300 |
| −550 | −500 | 0.4800 |
| −500 | −450 | 0.5300 |
| −450 | −400 | 0.5800 |
| −400 | −350 | 0.6300 |
| −350 | −300 | 0.6800 |
| −300 | −250 | 0.7300 |
| −250 | −200 | 0.7800 |
| −200 | −175 | 0.8175 |
| −175 | −150 | 0.8425 |
| −150 | −125 | 0.8675 |
| −125 | −100 | 0.8925 |
| −100 | −80 | 0.9142 |
| −80 | −60 | 0.9342 |
| −60 | −40 | 0.9542 |
| −40 | −20 | 0.9742 |
| −20 | 0 | 0.9942 |
| 0 | 20 | 1.0142 |
| 20 | 40 | 1.0342 |
| 40 | 60 | 1.0542 |
| 60 | 80 | 1.0742 |
| 80 | 100 | 1.0942 |
| 100 | 125 | 1.0827 |
| 125 | 150 | 1.0977 |
| 150 | 175 | 1.1127 |

TABLE 4-continued

Conversion of CT value and mass density HUL and HUU being the lower and upper limits of CT value, respectively

| $HU_L$ | $HU_U$ | $\rho$ (g/cm³) |
|---|---|---|
| 175 | 200 | 1.1277 |
| 200 | 225 | 1.1427 |
| 225 | 250 | 1.1577 |
| 250 | 275 | 1.1727 |
| 275 | 300 | 1.1877 |
| 300 | 325 | 1.2027 |
| 325 | 350 | 1.2177 |
| 350 | 375 | 1.2327 |
| 375 | 400 | 1.2477 |
| 400 | 425 | 1.2627 |
| 425 | 450 | 1.2777 |
| 450 | 475 | 1.2927 |
| 475 | 500 | 1.3077 |
| 500 | 525 | 1.3227 |
| 525 | 550 | 1.3377 |
| 550 | 575 | 1.3527 |
| 575 | 600 | 1.3677 |
| 600 | 625 | 1.3827 |
| 625 | 650 | 1.3977 |
| 650 | 675 | 1.4127 |
| 675 | 700 | 1.4277 |
| 700 | 725 | 1.4427 |
| 725 | 750 | 1.4577 |
| 750 | 775 | 1.4727 |
| 775 | 800 | 1.4877 |
| 800 | 825 | 1.5027 |
| 825 | 850 | 1.5177 |
| 850 | 875 | 1.5327 |
| 875 | 900 | 1.5477 |
| 900 | 925 | 1.5627 |
| 925 | 950 | 1.5777 |
| 950 | 975 | 1.5927 |
| 975 | 1000 | 1.6077 |
| 1000 | 1050 | 1.6302 |
| 1050 | 1100 | 1.6602 |
| 1100 | 1150 | 1.6902 |
| 1150 | 1200 | 1.7202 |
| 1200 | 1250 | 1.7502 |
| 1250 | 1300 | 1.7802 |
| 1300 | 1350 | 1.8102 |
| 1350 | 1400 | 1.8402 |
| 1400 | 1450 | 1.8702 |
| 1450 | 1500 | 1.9002 |
| 1500 | 1550 | 1.9302 |
| 1550 | 1600 | 1.9602 |
| 1600 | 1650 | 1.9902 |
| 1650 | 1700 | 2.0202 |
| 1700 | 1750 | 2.0502 |
| 1750 | 1800 | 2.0802 |
| 1800 | 1850 | 2.1102 |
| 1850 | 1900 | 2.1402 |
| 1900 | 1950 | 2.1702 |
| 1950 | 2000 | 2.2002 |
| 2000 | | 2.2152 |

The method uses the mass ratios of known elements of a tissue to calculate the mass ratios of elements of other tissues by using the computed tomography image data, so that when making a voxel phantom, more different CT data may be considered, providing more tissue types, making the phantom more realistic to the real situation. The phantom may be used in a treatment planning system based on Monte Carlo algorithm to specify the correct physical action data, such as the linear attenuation coefficient of photons, the effective cross section of neutrons, and the mass blocking power of charged particles (protons, electrons or other charged particles), in Monte Carlo calculations through a large amount of mass ratios of elements of tissues, and provide a near-real particle migration environment.

Although the illustrative embodiments of the present invention have been described above in order to enable those skilled in the art to understand the present invention, it should be understood that the present invention is not to be limited the scope of the embodiments. For those skilled in the art, as long as various changes are within the spirit and scope as defined in the present invention and the appended claims, these changes are obvious and within the scope of protection claimed by the present invention.

What is claimed is:

1. A method for establishing a geometric model based on a medical image, comprising:
   reading data of the medical image;
   defining a type of a tissue according to a process for analyzing elements and mass ratios of the elements of the tissue based on the medical image, wherein the process comprises approximating the tissue having unknown elements and mass ratios of the unknown elements thereof using the data of the medical image corresponding to a tissue having known elements and mass ratios of the known elements thereof;
   determining a quantity of tissue clusters of the tissue;
   defining a tissue density of the tissue by a conversion relationship between the data of the medical image and density values;
   establishing a three-dimensional (3D) encoding matrix with information about the tissue and the tissue density; and
   generating the geometric model based on the 3D encoding matrix.

2. The method according to claim 1, wherein the data of the medical image is related to a photon linear attenuation coefficient, and an effective linear attenuation coefficient of the tissue having the known elements and the mass ratios of the known elements thereof is obtained from the data of the medical image.

3. The method according to claim 2, wherein the tissue having the unknown elements and the mass ratios of the unknown elements thereof is approximated using the data of the medical image corresponding to the tissue having the known elements and the mass ratios of the known elements thereof by:
   calculating an average linear attenuation coefficient $\mu_i$ under a beam of the medical image by weighting a plurality of photon linear attenuation coefficients of elements provided by NIST using a beam energy spectrum of the medical image;
   obtaining an efficiency weighting factor C as a product of a detector efficiency and an additive factor of the medical image, and correcting a linear attenuation coefficient $\mu_{tissue}$, tissue of each of a plurality of known tissues by the efficiency weighting factor C to obtain an effective linear attenuation coefficient $\mu_{eff}$, of each of the known tissues, wherein the tissue having the known elements is one of the known tissues, and $\mu_{eff} = C \cdot \mu_{tissue} = C \cdot \Sigma_{i=1}^{n} m_i \mu_i$; and
   obtaining a mass ratio distribution of chemical elements $m_i$ in a living organism corresponding to each of the data of the medical image by a derivation algorithm using the mass ratios of the known elements of a tissue with similar data of the medical image as an initial hypothesis.

4. The method according to claim 3, wherein the data of the medical image includes CT values, and the relationship between a Hounsfield unit (HU) of each of the CT values and the effective linear attenuation coefficient $\mu_{eff}$ is HU=1000 ($\mu_{eff}/\mu_{water}$=1).

5. The method according to claim 4, wherein the CT values are grouped into a plurality of groups with a size of n, and the CT values range from −100 to +1530 are divided into 1630/n groups.

6. The method according to claim 3, wherein the derivation algorithm is a maximum approximation algorithm.

7. The method according to claim 1, being applied to neutron capture therapy, and further comprising:
assigning a Boron-10 concentration; and
establishing the 3D encoding matrix with information of the Boron-10 concentration.

8. The method according to claim 1, wherein the quantity of the tissue clusters is a quantity of the tissue clusters manually defined by a user, plus a quantity of four tissue clusters, fourteen tissue clusters or seventy tissue clusters already existing in a database or a quantity of 163 tissue clusters determined by the process.

9. The method according to claim 8, further comprising:
establishing a 3D tissue encoding matrix; and
establishing a 3D density encoding matrix.

10. The method according to claim 1, wherein the geometric model comprises a lattice card, a cell card, a surface card and a material card required by an input file of MCNP software.

11. A method for establishing a geometric model based on a medical image, the method comprising:
reading data of the medical image;
defining or reading a region of interest (ROI) boundary;
determining whether each of a plurality of medical image voxels in the data of the medical image is within the ROI boundary;
when one of the medical image voxels is determined to be within the ROI boundary, performing manually defining a type and a density of a ROI tissue by assigning a particular tissue and the density to the one of the medical image voxels within the ROI boundary, or performing:
automatically defining the type of the ROI tissue according to a a process for analyzing elements and mass ratios of the elements of the ROI tissue based on the medical image, wherein the process comprises approximating the ROI tissue having unknown elements and mass ratios of the unknown elements thereof using the data of the medical image corresponding to a tissue having known elements and mass ratios of the known elements thereof,
determining a quantity of tissue clusters of the ROI tissue, and
automatically defining the density of the ROI tissue by a conversion relationship between the data of the medical image and density values;
when one of the medical image voxels is determined not to be within the ROI boundary, performing:
automatically defining a type of a non-ROI tissue according to the process,
determining a quantity of tissue clusters of the non ROI tissue, and
automatically defining the tissue density of the non-ROI tissue by the conversion relationship between the data of the medical image and the density values;
establishing a three-dimensional (3D) encoding matrix with information about the ROI tissue or the non-ROI tissue and the tissue density thereof; and
generating the geometric model based on the 3D encoding matrix.

12. The method according to claim 11, wherein the data of the medical image is related to a photon linear attenuation coefficient, and an effective linear attenuation coefficient of the tissue having known mass ratios of elements thereof is obtained from the data of the medical image.

13. The method according to claim 12, wherein the ROI tissue having the unknown elements and the mass ratios of the unknown elements thereof is approximated using the data of the medical image corresponding to the tissue having the known elements and the mass ratios of the known elements thereof comprises:
calculating an average linear attenuation coefficient $\mu_i$ under a beam of the medical image by weighting a plurality of photon linear attenuation coefficients of elements provided by NIST using a beam energy spectrum of the medical image;
obtaining an efficiency weighting factor C as a product of a detector efficiency and an additive factor of the medical image, and correcting a linear attenuation coefficient $\mu_{tissue}$ tissue of each of a plurality of known tissues by the efficiency weighting factor C to obtain an effective linear attenuation coefficient $\mu_{eff}$ of each of the known tissues, wherein the tissue having the known elements is one of the known tissues, and $\mu_{eff} = C \cdot \mu_{tissue} = C \cdot \Sigma_{i=1}^{n} m_i \mu_i$; and
obtaining a mass ratio distribution of chemical elements $m_i$ in a living organism corresponding to each of the data of the medical image by a derivation algorithm using the mass ratios of elements of a tissue with similar data of the medical image as an initial hypothesis.

14. The method according to claim 13, wherein the data of the medical image includes CT values, and the relationship between a Hounsfield unit (HU) of each of the CT values and the effective linear attenuation coefficient $\mu_{eff}$ is $HU = 1000(\mu_{eff}/\mu_{water} - 1)$.

15. The method according to claim 14, wherein the CT values are grouped into a plurality of groups with a size of n, and the CT values range from −100 to +1530 are divided into 1630/n groups.

16. The method according to claim 13, wherein the derivation algorithm is a maximum approximation algorithm.

17. The method according to claim 11, being applied to neutron capture therapy and further comprising:
assigning a Boron-10 concentration; and
establishing the 3D encoding matrix with information of the Boron-10 concentration.

18. The method according to claim 11, wherein the quantity of the tissue clusters is a quantity of the tissue clusters manually defined by a user, plus a quantity of four tissue clusters, fourteen tissue clusters or seventy tissue clusters already existing in a database or a quantity of 163 tissue clusters determined by the process.

19. The method according to claim 18, further comprising:
establishing a 3D tissue encoding matrix; and
establishing a 3D density encoding matrix.

20. The method according to claim 11, wherein the geometric model comprises a lattice card, a cell card, a surface card and a material card required by an input file of MCNP software.

* * * * *